(12) United States Patent
Kobayashi et al.

(10) Patent No.: US 6,540,894 B2
(45) Date of Patent: Apr. 1, 2003

(54) PHOSPHATE ION SELECTIVE ELECTRODE AND MANUFACTURING METHOD THEREOF

(75) Inventors: Takeshi Kobayashi, Kyoto (JP); Yasukazu Iwamoto, Kyoto (JP)

(73) Assignee: Horiba, LTD, Kyoto (JP)

( * ) Notice: Subject to any disclaimer, the term of this patent is extended or adjusted under 35 U.S.C. 154(b) by 77 days.

(21) Appl. No.: 09/906,084

(22) Filed: Jul. 17, 2001

(65) Prior Publication Data
US 2002/0043459 A1 Apr. 18, 2002

(30) Foreign Application Priority Data

Sep. 13, 2000 (JP) .......................................... 2000-278477

(51) Int. Cl.[7] .............................................. G01N 27/26
(52) U.S. Cl. ....................................... 204/419; 204/416
(58) Field of Search .................................. 204/416, 419

(56) References Cited

U.S. PATENT DOCUMENTS

| | | | | |
|---|---|---|---|---|
| 4,083,764 A | * | 4/1978 | Van De Leest et al. | 204/419 |
| 4,735,692 A | * | 4/1988 | Arnold et al. | 204/418 |
| 5,180,481 A | * | 1/1993 | Carey | 204/416 |
| 5,415,746 A | * | 5/1995 | Cha | 204/418 |
| 5,417,836 A | * | 5/1995 | Masuda et al. | 204/419 |

* cited by examiner

*Primary Examiner*—Bruce F. Bell
(74) *Attorney, Agent, or Firm*—Sughrue Mion, PLLC

(57) ABSTRACT

A phosphate ion selective electrode, with which the detection limit is made small to enable measurement of phosphate ion concentrations of down to low concentration, and a method of manufacturing the abovementioned phosphate ion selective electrode, wherein a sensing membrane 1 of an ion selective electrode A is comprised of a solid membrane having a slightly soluble metal salt as the main component thereof.

3 Claims, 2 Drawing Sheets

US 6,540,894 B2

PHOSPHATE ION SELECTIVE ELECTRODE AND MANUFACTURING METHOD THEREOF

BACKGROUND OF THE INVENTION

1. Field of the Invention

This invention concerns a phosphate ion selective electrode, which enables selective measurement of phosphate ion concentration, which is regarded as an important indicator of eutrophication in lakes, marshes, etc., and a method of manufacturing this phosphate ion selective electrode.

2. Description of the Prior Art

An ion selective electrode (also referred to as "ion electrode") responds selectively to an ion for which the electrode is designed to analyze and is used to measure ion concentrations, ion activities, etc.

Such an ion electrode responds to a specific ion and indicates a potential difference across a reference electrode in accordance with the ion concentration, thereby enabling the quantification of the targeted ion. For example, with a negative ion selective electrode, the Nernst equation holds between the activity $a_x$ of the measured ion ($X^{n-}$) and the potential difference E (mV) indicated by the negative ion selective electrode, and at 25° C., the following proportional relationship holds between the potential difference E and the logarithm of the activity $a_x$:

$$E = E^0 (\text{reference potential difference}(mV) \text{ of the system}) + \frac{59.16}{n} \log a_x$$

The activity $a_x$ of the targeted ion can thus be calculated simply from the measured value of the potential difference E.

As a prior-art ion electrode that responds to phosphate ions, there is the liquid membrane electrode, in which an ionophore is impregnated and fixed in a polymer substance. However, this type of electrode generally has a high detection limit and is poor in stability.

On the other hand, a solid membrane electrode, with which the sensing membrane is comprised of a solid membrane having the slightly soluble phosphate salt of zinc phosphate as the main component, has also been proposed (refer to Japanese Unexamined Patent Publication No. 130262 of 1992). However the detection limit of this type of electrode is too high for measurement of phosphate ion concentrations down to low concentrations.

SUMMARY OF THE INVENTION

In order to achieve the above object, this invention provides a phosphate ion selective electrode comprising a sensing membrane made of a solid membrane having a slightly soluble metal salt as the main component.

Another mode of this invention provides a phosphate ion selective electrode manufacturing method characterized in that the slightly soluble metal salt of aluminum phosphate is used as the main component, the powder of this aluminum phosphate is subject to hot press forming, and the solid membrane that is obtained is used as the sensing membrane.

This invention provides the effect that a phosphate ion selective electrode, which is lower in detection limit and enables measurements down to lower concentrations in comparison to prior-art sensing membranes, can be provided.

DETAILED DESCRIPTION OF THE PREFERRED EMBODIMENT

An embodiment of this invention shall now be described with reference to the drawings.

Figure 1:
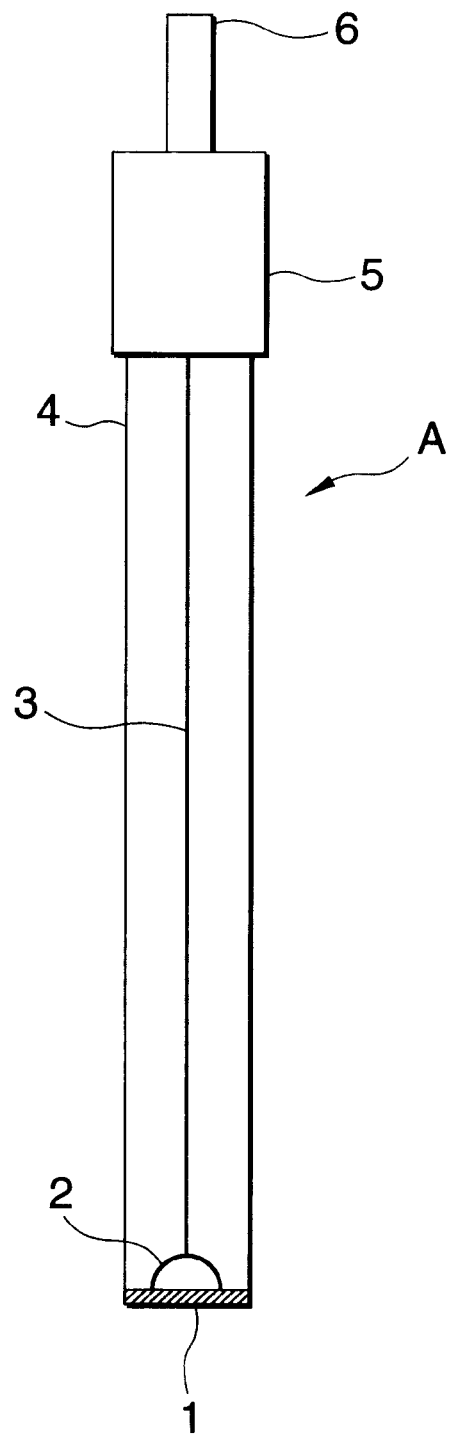
FIG. 1 is an explanatory arrangement diagram, which shows an embodiment of this invention.
Figure 2:
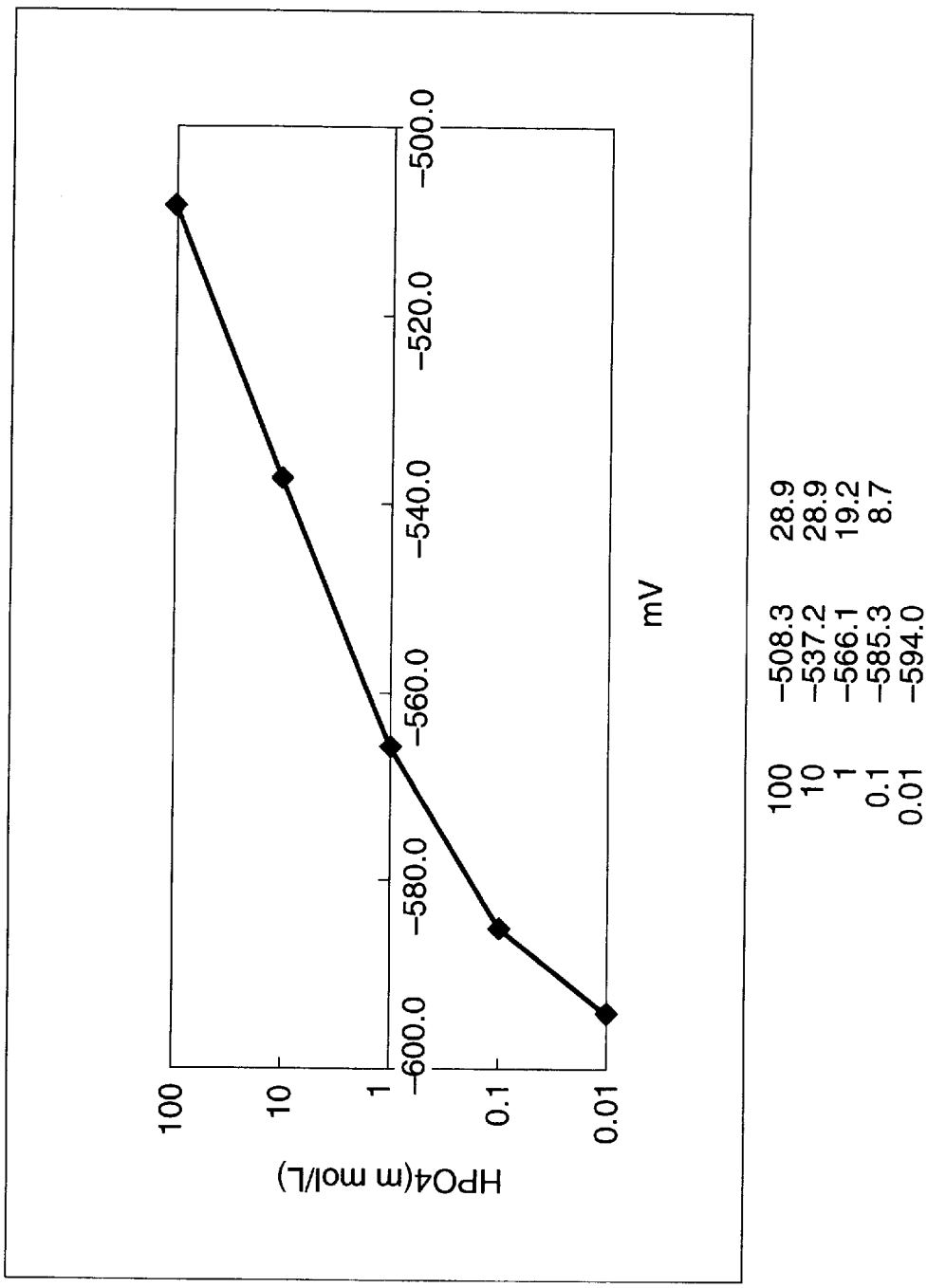
FIG. 2 is a phosphate ion concentration vs. electric potential characteristics diagram of the abovementioned embodiment.

FIG. 1 shows the overall arrangement of a phosphate ion selective electrode of an embodiment of this invention and FIG. 2 shows a phosphate ion calibration curve.

In FIG. 1, reference numeral 1 is a sensing membrane, which is formed as a solid membrane made by heat press forming (hot pressing) a mixture of aluminum phosphate (example of a slightly soluble metal salt) and aluminum metal.

Reference numeral 2 is a conductive adhesive agent, which electrically connects solid membrane 1 and a lead wire 3 inside a supporting tube 4. Phosphate ion selective electrode A is formed by sealing the upper end of supporting tube 4 by cap 5 with solid membrane 1 being supported at the lower end of supporting tube 4. Reference numeral 6 is a conductor wire.

The procedure for manufacturing solid membrane 1 shall now be described.

(1) First, an aluminum phosphate solution, prepared by dissolving aluminum phosphate in hot water, is refined by filtration to eliminate the sodium phosphate contained in the aluminum phosphate solution. The sodium phosphate is eliminated from the aluminum phosphate solution to prevent the dissolution of phosphate ions from sensing membrane 1. In the present embodiment for example, 10 g of aluminum phosphate is dissolved in 1000 milliliters of hot water. Here it is preferable to perform refining by filtration not just once but three times repeatedly to increase the purity of aluminum phosphate.

(2) Next, the aluminum phosphate solution from which sodium phosphate has been eliminated is dried. The temperature for drying is preferably 110 to 115° C. and the drying time is preferably 24 hours.

(3) Subsequently, the dried aluminum phosphate and aluminum powder (aluminum metal) are placed and mixed in a mortar so that the total amount will for example be 20 g and grinding and mixing are performed.

(4) In the final step, the mixed and ground substance (powder) is subject to heat press forming (hot pressing) to obtain the sensing membrane 1, which is formed as a solid membrane of predetermined size. The temperature for hot press forming is preferably 160° C., the pressure is preferably 5 ton/cm², and the pressing time is preferably 20 minutes.

Then as has been described above, assembly is performed by adhering the solid membrane 1, which has been obtained, to lead wire 3 using conductive adhesive agent 2 to obtain phosphate ion selective electrode A.

The conditioning of this phosphate ion selective electrode A is performed by immersing the outer part of sensing membrane 1 in an $Na_2HPO_4$ solution of 0.001 moles/liter overnight and thereafter use is made of the phosphate ion selective electrode A.

This phosphate ion selective electrode A responds to phosphate ions and indicates a potential difference across a reference electrode in correspondence to the phosphate ion concentration, thereby enabling quantitative determination of the phosphate ion concentration.

The phosphate ion selective electrode A of this invention is arranged as a so-called type 2 electrode and also enables detection of the aluminum ion concentration by use of the redox potential of aluminum metal. That is, with the phosphate ion selective electrode of this invention, the dissolution equilibrium of aluminum phosphate is determined by phosphate and also captures changes in the aluminum ion concentration at the same time.

Next, the relationship between electric potential and phosphate ion concentration was measured using a reference electrode, ionometer, etc. The evaluation results are shown in FIG. 2.

From FIG. 2, it can be understood that the phosphate ion selective electrode A of this invention complies with the Nernst equation that establishes a proportional relationship between the potential difference (mV) and the logarithm of $HPO_4$ (mmol/l) (activity of phosphate ion). It has thus been clarified that the phosphate ion selective electrode A of this invention responds selectively to phosphate ions.

Furthermore with regard to the detection limit (mol/l), the phosphate ion selective electrode A of this invention exhibits the following characteristics in comparison to a phosphate ion selective electrode B of the type described in the abovementioned Japanese Unexamined Patent Publication No. H04-130262 (1992).

That is, if s is the solubility of zinc phosphate $Zn_3(PO_4)_2$, which is the slightly soluble phosphate salt used in the sensing membrane of the abovementioned phosphate ion selective electrode B and $k_{sp}$ is the solubility product, $k_{sp}=9.1\times10^{-33}=[Zn]^3[PO_4]^2$, and $s=3.91\times10^{-7}$, and thus theoretically, detection down to a concentration of $3.91\times10^{-7}$(mol/l) is possible.

On the other hand with the phosphate ion selective electrode A of this invention, aluminum phosphate ($AlPO_4$) is used as the slightly soluble metal salt that is the main component, and thus if s' is the solubility of aluminum phosphate ($AlPO_4$) and $k'_{sp}$ is the solubility product, $k'_{sp}=1.3\times10^{-20}=[Al][PO_4]$ and $s'=1.14\times10^{-10}$, and thus theoretically, detection down to a concentration of $1.14\times10^{-10}$(mol/l) is possible.

That is, the phosphate ion selective electrode A of this invention enables measurements down to lower concentrations in comparison to the above-described phosphate ion selective electrode B.

That is, since with this invention, an electrode structure is employed with which a solid membrane 1 of predetermined size, obtained by press forming a powder having a slightly soluble metal salt of low solubility as the main component, is used as the sensing membrane, the detection limit of the phosphate ion selective electrode A of this invention can be made smaller than the above-described phosphate ion selective electrode B, which has a solid membrane (sensing membrane) having a slightly soluble phosphate salt (metal salt) of higher salt solubility than the abovementioned slightly soluble metal.

This invention has been made in view of the above and an object thereof is to provide a phosphate ion selective electrode, with which the detection limit is made small to enable measurement of phosphate ion concentrations of down to low concentration, and a method of manufacturing the abovementioned phosphate ion selective electrode.

What is claimed is:

1. A phosphate ion selective electrode comprising:

a sensing membrane made of a solid membrane having a slightly soluble metal salt as the main component thereof, wherein said slightly soluble metal salt is aluminum phosphate.

2. A phosphate ion selective electrode as claimed in claim 1, wherein the sensing substances that form said sensing membrane also include aluminum metal.

3. A phosphate ion selective electrode manufacturing method comprising the steps of:

using a slightly soluble metal salt of aluminum phosphate as a main component;

heat press forming powder of the aluminum phosphate; and using the solid membrane thus obtained as a sensing membrane.

* * * * *